US005658944A

United States Patent [19]

Chapman, Jr. et al.

[11] Patent Number: 5,658,944
[45] Date of Patent: Aug. 19, 1997

[54] ANTI-ATHEROSCLEROTIC ARYL COMPOUNDS

[75] Inventors: James Mood Chapman, Jr., Columbia, S.C.; Roy Lee Hawke, Cary, N.C.; Karl Witold Franzmann, Beckenham; Kevin Julian O'Connor, Brenchley, both of United Kingdom

[73] Assignee: The University of South Carolina, Columbia, S.C.

[21] Appl. No.: 421,997

[22] Filed: Apr. 14, 1995

Related U.S. Application Data

[62] Division of Ser. No. 962,068, Oct. 16, 1992, abandoned, which is a continuation of Ser. No. 805,236, Dec. 11, 1991, abandoned.

[30] Foreign Application Priority Data

Dec. 12, 1990 [GB] United Kingdom ............... 9027023

[51] Int. Cl.$^6$ .................. A61K 31/27; C07C 229/00; C07C 275/02; C07C 233/01
[52] U.S. Cl. .................. 514/478; 514/534; 514/535; 514/576; 514/588; 514/617; 514/619; 560/34; 560/39; 560/43; 560/61; 562/444; 562/439; 562/457; 562/471; 564/48; 564/161; 564/163; 564/169
[58] Field of Search .................. 562/439, 444, 562/457, 471; 560/34, 39, 43, 61; 564/48, 161, 163, 169; 514/478, 534, 535, 576, 588, 617, 619

[56] References Cited

U.S. PATENT DOCUMENTS

| | | | |
|---|---|---|---|
| 4,387,106 | 6/1983 | DeVries et al. | 562/437 |
| 4,397,868 | 8/1983 | DeVries | 562/437 |
| 4,623,662 | 11/1986 | Devries | 562/437 |

FOREIGN PATENT DOCUMENTS

| | | |
|---|---|---|
| 0 370 740 A1 | 5/1990 | European Pat. Off. . |
| 2614045 | 10/1977 | Germany . |
| 88/10113 | 12/1988 | WIPO . |
| 89/12622 | 12/1989 | WIPO . |

OTHER PUBLICATIONS

Lalezari, et al., J. Med. Chem. 32(10), 2352–7 1989.
European Search Report.
J. Med. Chem., vol. 32, pp. 2352–2357, 1989.
Proc. Natl. Acad. Sci., vol. 85, pp. 6117–6121, 1988.

*Primary Examiner*—Joseph Conrad
*Attorney, Agent, or Firm*—Michael A. Mann

[57] ABSTRACT

The present invention is concerned with compounds of formula (I)

$$Ar-D-CO-E\underset{G}{\overset{J}{<}}\!\!\!-\!\!\!\bigcirc\!\!\!-\!\!O-(CH_2)_n-\underset{R^1}{\overset{R}{\mid}}-K \quad (I)$$

wherein
  Ar is a mono- or bicyclic aromatic group optionally containing one or two heteroatoms independently selected from nitrogen, oxygen and sulphur, said group being optionally substituted by one or more atoms or groups independently selected from halogen, nitro, amino, —NRR$^1$ where R and R$^1$ are independently selected from hydrogen, C$_{1-8}$ alkyl and C$_{1-8}$ alkanoyl, cyano, carboxyalkoxy, alkoxycarbonylalkoxy, C$_{1-8}$ alkyl (including cycloalkyl and cycloalkylalkyl), C$_{1-8}$ alkoxy (including cycloalkoxy and cycloalkylalkoxy), C$_{1-8}$ thioalkyl, said alkyl, alkoxy and/or thioalkyl group(s) being optionally substituted by one or more halogen atoms, aryl, aryloxy, aralkyl and aralkyloxy, said aryl, aryloxy, aralkyl and/or aralkyloxy group(s) being optionally substituted by one or more atoms or groups independently selected from halogen, alkyl, alkoxy, alkanoyl, hydroxyalkyl, perfluoroalkyl, perfluoroalkoxy, carboxyalkoxy, alkoxycarbonylalkoxy, and C$_{3-8}$ polyether groups containing from one to three oxygen atoms;
  D is —CH$_2$—, —NH—, or —O—;
  E is —N< or —CH<;
  G is hydrogen, C$_{1-12}$ straight, branched, or cyclic alkyl, or aralkyl, said aralkyl group being optionally substituted by one or more atoms or groups independently selected from halogen, amino, N-(C$_{1-6}$ alkyl)amino, N,N-di (C$_{1-6}$ alkyl)amino, C$_{1-6}$ alkyl and C$_{1-6}$ alkoxy, or a C$_{3-8}$ polyether group containing one to three oxygen atoms;
  J is a bond or C$_{1-6}$ straight or branched alkylene;
  n is an integer of from 0 to 10;
  R and R$^1$ are as hereinbefore defined; and
  K is —CH$_2$OH, —CHO, —CONHCH$_2$CONH$_2$, —CONH(C$_{1-6}$ alkyl), —OC(C$_{1-4}$ alkyl)$_2$ OCOheteroaryl, —CO$_2$R$^2$ where R$^2$ is hydrogen, C$_{1-8}$ alkyl, aryl, heteroaryl, aralkyl, heteroaralkyl, or a C$_{3-8}$ polyether group containing from one to three oxygen atoms, or —CONHAr' where Ar' is phenyl optionally substituted by one or more atoms or groups selected from fluorine, nitro, —NRR$^1$ where R and R$^1$ are as hereinbefore defined, C$_{1-6}$ alkyl and C$_{1-6}$ alkoxy, said alkyl and/or alkoxy group(s) being optionally substituted at the terminal carbon by —CO$_2$R$^3$ where R$^3$ is C$_{1-6}$ alkyl;
and their physiologically functional derivatives, with processes for their preparation, with medicaments containing them and with their use as therapeutic agents, particularly in the prophylaxis and treatment of atherosclerosis.

5 Claims, No Drawings

ANTI-ATHEROSCLEROTIC ARYL COMPOUNDS

This is a divisional of application Ser. No. 07/962,068 filed on Oct. 16, 1992 now abandoned which is a continuation of 07/805,236 Dec. 11, 1991 now abandoned.

The present invention is concerned with a novel genus of diaryl compounds, with processes for their preparation, with medicaments containing them and with their use as therapeutic agents, particularly in the prophylaxis and treatment of atherosclerosis.

The enzyme acyl coenzyme A—cholesterol acyl transferase (ACAT) is known to be involved in the intestinal absorption of cholesterol and in the accumulation of cholesterol as cholesterol esters in the arterial wall. Thus compounds which inhibit ACAT have the potential of demonstrating both potent hypocholesterolaemic activity and a decrease in arterial cholesterol deposition.

A group of compounds known collectively as 'fibrates' which give rise to a modest decrease in LDL-cholesterol, a significant decrease in triglycerides and a marked elevation of HDL-cholesterol in the plasma have been found useful in the treatment of Type IIA, IIB, III, IV and V hyperlipidaemias. The increase in the level of HDL-cholesterol is particularly important since it facilitates the removal of free cholesterol from the arterial wall for return to the liver ('reverse cholesterol transport').

It follows that a drug combining the hypocholesterolaemic/anti-atherosclerotic properties of an ACAT inhibitor with hypolipidaemic/HDL-enhancing properties would be particularly useful in the prophylaxis and treatment of atherosclerosis, the enhanced HDL-cholesterol level induced giving rise to an increase in the capacity of the reverse cholesterol transport mechanism to remove the free cholesterol resulting from ACAT inhibition in the arterial wall. Such a drug would be especially beneficial to Type IIA and Type III patients having both high serum cholesterol and triglyceride levels who are at particular risk of contracting coronary heart disease.

On the basis of the foregoing, we have disovered a series of novel compounds having potential hypolipidaemic/hypocholesterolaemic activity.

According to the present invention, therefore, there is provided a compound of formula (I)

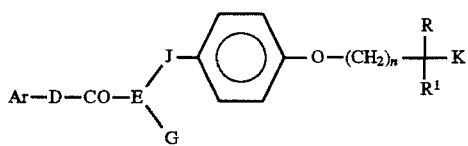

wherein

Ar is a mono- or bicyclic aromatic group optionally containing one or two heteroatoms independently selected from nitrogen, oxygen and sulphur, said group being optionally substituted by one or more atoms or groups independently selected from halogen, nitro, amino, —$NRR^1$ where R and $R^1$ are independently selected from hydrogen, $C_{1-8}$ alkyl and $C_{1-8}$ alkanoyl, cyano, carboxyalkoxy, alkoxycarbonylalkoxy, $C_{1-8}$ alkyl (including cycloalkyl and cycloalkylalkyl), $C_{1-8}$ alkoxy (including cycloalkoxy and cycloalkylalkoxy), $C_{1-8}$ thioalkyl, said alkyl, alkoxy and/or thioalkyl group(s) being optionally substituted by one or more halogen atoms, aryl, aryloxy, aralkyl and aralkyloxy, said aryl, aryloxy, aralkyl and/or aralkyloxy group(s) being optionally substituted by one or more atoms or groups independently selected from halogen, alkyl, alkoxy, alkanoyl, hydroxyalkyl, perfluoroalkyl, perfluoroalkoxy, carboxyalkoxy, alkoxycarbonylalkoxy, and $C_{3-8}$ polyether groups containing from one to three oxygen atoms;

D is —$CH_2$—, —NH— or —O—;

E is —N< or —CH<;

G is hydrogen, $C_{1-12}$ straight, branched, or cyclic alkyl, or aralkyl, said aralkyl group being optionally substituted by one or more atoms or groups independently selected from halogen, amino, N-($C_{1-6}$ alkyl)amino, N,N-di ($C_{1-6}$ alkyl)amino, $C_{1-6}$ alkyl and $C_{1-6}$ alkoxy, or a $C_{3-8}$ polyether group containing one to three oxygen atoms;

J is a bond or $C_{1-6}$ straight or branched alkylene;

n is an integer of from 0 to 10;

R and $R^1$ are as hereinbefore defined; and

K is —$CH_2OH$, —CHO, —$CONHCH_2CONH_2$, —$CONH(C_{1-6}$ alkyl), —$OC(C_{1-4}$ alkyl$)_2$ OCOheteroaryl, —$CO_2R_2$ where $R^2$ is hydrogen, $C_{1-8}$ alkyl, aryl, heteroaryl, aralkyl, heteroaralkyl, or a $C_{3-8}$ polyether group containing from one to three oxygen atoms, or —CONHAr' where Ar' is phenyl optionally substituted by one or more atoms or groups selected from fluorine, nitro, —$NRR^1$ where R and $R^1$ are as hereinbefore defined, $C_{1-6}$ alkyl and $C_{1-6}$ alkoxy, said alkyl and/or alkoxy group(s) being optionally substituted at the terminal carbon by —$CO_2R^3$ where $R^3$ is $C_{1-6}$ alkyl;

and salts and physiologically functional derivatives thereof.

Salts of compounds of formula (I) suitable for use in medicine are those which are physiologically acceptable. However, non-physiologically acceptable salts are within the scope of the present invention for use as intermediates in the preparation of the compounds of the invention and their physiologically acceptable salts and physiologically functional derivatives.

The "physiologically functional derivatives" referred to herein are compounds which are converted in vivo to a compound of formula (I) or one of its physiologically acceptable salts.

Preferred compounds of formula (I) having particularly good ACAT inhibiting/fibrate-like properties include those wherein Ar is phenyl or naphthyl substituted by one or more atoms or groups independently selected from halogen, $C_{1-8}$ alkyl, $C_{1-8}$ alkoxy (including cycloalkylalkoxy), said alkyl and/or alkoxy group(s) being optionally substituted by one or more halogen atoms, $C_{1-8}$ thioalkyl, aryl, aryloxy and aralkoxy, said aralkoxy group being optionally substituted by alkyl, alkoyl, or hydroxyalkyl;

D is —NH—or —O—;

E is —N<;

G is $C_{5-8}$ straight or branched alkyl, (4-halophenyl)$C_{1-3}$ alkyl, or [4-di($C_{1-6}$ alkyl)aminophenyl]$C_{1-3}$ alkyl;

J is $C_{1-3}$ alkylene;

n is an integer of from 0 to 4;

R and $R^1$ are respectively hydrogen and $C_{1-4}$ alkyl or are both $C_{1-4}$ alkyl; and K is —$CO_2R^2$ where $R^2$ is hydrogen or $C_{1-4}$ alkyl, or —$CH_2OH$;

and physiologically acceptable salts and physiologically functional derivatives thereof.

Particularly preferred compounds of the invention are 2-(4-{2-[3-(2,4-dimethoxyphenyl)-1-heptylureido]ethyl)}phenoxy)-2-methylpropionic acid, 2-(4-{2-[3(2,4- difluorophenyl)-1-heptylureido]ethyl}phenoxy)-2-methylpropionic acid, 2-(4-[3-(2,4-dimethoxyphenyl)-1-heptylureidomethyl]phenoxy)-2-methyl-propionic acid, 2-{4-[1-heptyl-3-(2,4,6-trichlorophenyl)ureidomethyl] phenoxy}-2-methylpropionic acid, 2-{4-[1-(3,3-dimethylbutyl)-3-(2,4-dimethoxyphenyl)ureidomethyl] phenoxy}-2-methylpropionic acid, 3-(2,4-dimethoxyphenyl)-1-heptyl-1-[4-(2-hydroxy-1-methylethoxy)benzyl]urea, 3-(2,4-dimethylphenyl)-1-heptyl-1-[4-(5-hydroxy-4,4-dimethylpentyloxy)benzyl]urea and their physiologically acceptable salts and physiologically functional derivatives.

According to further aspects of the invention, there are also provided:

(a) compounds of formula (I) and physiologically acceptable salts and physiologically functional derivatives thereof for use as a therapeutic agent;

(b) pharmaceutical formulations comprising a compound of formula (I) and/or one of its physiologically acceptable salts or physiologically functional derivatives and at least one pharmaceutical carrier;

(c) the use of a compound of formula (I) or of a physiologically acceptable salt or physiologically functional derivative thereof in the manufacture of a medicament for the prophylaxis or treatment of a clinical condition for which an ACAT inhibitor and/or a fibrate is indicated;

(d) a method for the prophylaxis or treatment of a clinical condition in a mammal, such as a human, for which an ACAT inhibitor and/or a fibrate is indicated which comprises the administration of a therapeutically effective amount of a compound of formula (I) or of a physiologically acceptable salt or physiologically functional derivative thereof to said mammal; and (e) processes for the preparation of compounds of formula (I) and salts and physiologically functional derivatives thereof.

With regard to aspects (a), (c) and (d), the ability of compounds of formula (I) to inhibit ACAT activity renders them useful as hypocholesterolaemics and for reducing the steady state concentration of cholesterol and cholesterol ester in the arterial wall. Similarly, the fibrate-like activity of compounds of formula (I) renders them useful as hypolipidaemics and for increasing the capacity of the reverse cholesterol transport mechanism to remove free cholesterol from the arterial wall.

On the basis of their ability to regress established atherosclerotic plaque and retard the build-up of fresh lesions, compounds of formula (I) find application in both the prophylaxis and treatment of atherosclerosis.

In view of their hypocholesterolaemic/hypolipidaemic properties, compounds of formula (I) and their physiologically acceptable salts and physiologically functional derivatives may also find application in the prophylaxis and treatment of pancreatitis, in 'shifting' the oxygen affinity of human haemoglobin to improve myocardial function, for example, in the treatment of ischaemic tissue, and as uricosuric agents for reducing elevated plasma uric acid levels arising from, for example, hypertriglyceridaemia. The compounds of the invention also exhibit calcium antagonism in the ileum, stimulate hepatic fatty acid oxidation in the liver and have the potential to lower plasma triglycerides and elevate plasma HDL-cholesterol.

Hereinafter all references to "compound(s) of formula (I)" refer to compound(s) of formula (I) as defined above including their physiologically acceptable salts and physiologically functional derivatives.

The amount of a compound of formula (I) which is required to achieve the desired biological effect will, of course, depend on a number of factors, for example, the specific compound chosen, the use for which it is intended, the mode of administration and the clinical condition of the recipient. In general, the daily dose will be in the range 5 mg to 1 g, for example, 10 mg per day. An intravenous dose may, for example, be in the range 100 mg to 1 g, which may conveniently be administered as an infusion of from 1 mg to 100 mg per minute. Infusion fluids suitable for this purpose may contain, for example, from 0.1 mg to 10 mg, typically 1 mg, per milliliter. Unit doses may contain, for example, from 100 mg to 1 g of the active compound. Thus ampoules for injection may contain, for example, from 100 mg to 500 mg and orally administrable unit dose formulations, such as tablets or capsules, may contain, for example, from 100 mg to 1 g, typically 200 mg. In the case of physiologically acceptable salts, the weights indicated above refer to the weight of the ion derived from the compound of formula (I).

For the prophylaxis or treatment of the conditions referred to above, the compounds of formula (I) may be used as the compound per se, but are preferably presented with an acceptable carrier in the form of a pharmaceutical formulation. The carrier must, of course, be acceptable in the sense of being compatible with the other ingredients of the formulation and must not be deleterious to the recipient. The carrier may be a solid or a liquid, or both, and is preferably formulated with the compound as a unit-dose formulation, for example, a tablet, which may contain from 0.05% to 95% by weight of the active compound. Other pharmacologically active substances may also be present including other compounds of formula (I) . The formulations of the invention may be prepared by any of the wellknown techniques of pharmacy consisting essentially of admixing the components.

The formulations include those suitable for oral, rectal, topical, buccal (e.g. sub-lingual) and parenteral (e.g. subcutaneous, intramuscular, intradermal, or intravenous) administration, although the most suitable route in any given case will depend on the nature and severity of the condition being treated and on the nature of the particular compound of formula (I) which is being used.

Formulations suitable for oral administration may be presented in discrete units, such as capsules, cachets, lozenges, or tablets, each containing a predetermined amount of a compound of formula (I); as a powder or granules; as a solution or a suspension in an aqueous or non-aqueous liquid; or as an oil-in-water or water-in-oil emulsion. As indicated, such formulations may be prepared by any suitable method of pharmacy which includes the step of bringing into association the active compound and the carrier (which may constitute one or more accessory ingredients). In general, the formulations are prepared by uniformly and intimately admixing the active compound with a liquid or finely divided solid carrier, or both, and then, if necessary, shaping the product. For example, a tablet may be prepared by compressing or moulding a powder or granules of the compound, optionally with one or more accessory ingredients. Compressed tablets may be prepared by compressing, in a suitable machine, the compound in a free-flowing form, such as a powder or granules optionally mixed with a binder, lubricant, inert diluent and/or surface active/dispersing agent(s). Moulded tablets may be made by moulding, in a suitable machine, the powdered compound moistened with an inert liquid diluent.

Formulations suitable for buccal (sub-lingual) administration include lozenges comprising a compound of formula (I) in a flavoured base, usually sucrose and acacia or tragacanth, and pastilles comprising the compound in an inert base such as gelatin and glycerin or sucrose and acacia.

Formulations of the present invention suitable for parenteral administration conveniently comprise sterile aqueous preparations of a compound of formula (I), preferably isotonic with the blood of the intended recipient. These preparations are preferably administered intravenously, although administration may also be effected by means of subcutaneous, intramuscular, or intradermal injection. Such preparations may conveniently be prepared by admixing the compound with water and rendering the resulting solution sterile and isotonic with the blood. Injectable compositions according to the invention will generally contain from 0.1 to 5% w/w of the active compound.

Formulations suitable for rectal administration are preferably presented as unit-dose suppositories. These may be prepared by admixing a compound of formula (I) with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include vaseline, lanoline, polyethylene glycols, alcohols, and combinations of two or more thereof. The active compound is generally present at a concentration of from 0.1 to 15% w/w of the composition, for example, from 0.5 to 2%.

Compounds of formula (I) may be prepared by conventional means well known to a skilled person. Thus compounds of formula (I) wherein D is —NH— and E is —N< may be prepared by reacting a compound of formula (II)

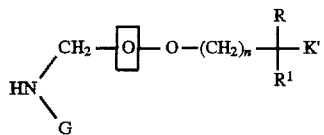  (II)

wherein n, G, J, R and R$^1$ are as hereinbefore defined and K' is as hereinbefore defined for K or is a suitably protected form thereof, with a compound of formula (III)

Ar—NCO  (III)

wherein Ar is as hereinbefore defined, typically in an aprotic polar solvent, for example, dichloromethane, and, if necessary, deprotecting the product.

Compounds of formula (II) wherein J is —CH$_2$— may be prepared by reacting a compound of formula (IV)

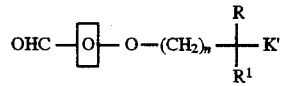  (IV)

wherein n, R, R$^1$ and K' are as hereinbefore defined, with a compound of formula (V)

G—NH$_2$  (V)

wherein G is as hereinbefore defined, typically by refluxing in a polar solvent, for example, ethanol, and reducing the resulting imine by, for example, hydrogenation over Pd/C.

Compounds of formula (IV) may be prepared by reacting commercially available 4-hydroxybenzaldehyde with a compound of formula (VI)

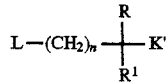  (VI)

wherein n, K', R and R$^1$ are as hereinbefore defined and L is a suitable leaving group, for example, bromo, typically by refluxing in a polar solvent, for example, ethanol, in the presence of potassium carbonate.

Compounds of formula (II) wherein J is C$_{2-6}$ straight or branched alkylene may be prepared by reacting a compound of formula (VII)

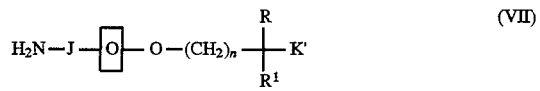  (VII)

wherein n, J, K', R and R$^1$ are as hereinbefore defined, with a compound of formula (VIII)

G'—CHO  (VIII)

wherein G' is as hereinbefore defined for G less a terminal methylene group, typically by mixing the two compounds together and reducing the resulting imine by, for example, hydrogenation over Pd/C.

Compounds of formula (VII) may be prepared by reacting a compound of formula (IX)

  (IX)

wherein J is as hereinbefore defined and P is a suitable protecting group, for example, benzyloxycarbonyl, with a compound of formula (VI) as hereinbefore defined, typically by refluxing in a polar solvent, for example, ethanol, in the presence of a base, for example, KOH, and deprotecting the product by, for example, in the case where P is benzyloxycarbonyl, hydrogenation over Pd/C.

Compounds of formula (IX) may be prepared from the corresponding amine (X) by treatment with a compound of formula (XI)

wherein L is a suitable leaving group, for example, chloro, and P is a suitable amino protecting group, for example, benzyloxycarbonyl.

Compounds of formula (III), (V), (VI), (VIII), (X) and (XI) are commercially available or may be prepared by methods well known to a skilled person or obtainable from the chemical literature.

Optional conversion of a compound of formula (I) to a corresponding salt may be effected by reaction with the appropriate acid or base. Optional conversion to a physiologically functional derivative may be carried out by methods well known to a skilled person or obtainable from the chemical literature.

For a better understanding of the invention, the following Examples are given by way of illustration.

SYNTHETIC EXAMPLE 1

Preparation of 2-(4-{[3-(2,4-dimethoxyphenyl)-1-heptylureido]methyl}phenoxy)-2-methylpropionic acid (a) Ethyl 2(4-formylphenoxy)-2-methylpropanoate 4Hydroxybenzaldehyde (24.4 g, Aldrich) was dissolved in absolute ethanol (470 ml) and anhy. K$_2$CO$_3$ (27.6 g) and ethyl 2-bromoisobutyrate (39.0 g, Aldrich) added. The resulting mixture was refluxed overnight, allowed to cool and the solvent removed in vacuo. The residue was suspended in water (300 ml) and extracted with CH$_2$Cl$_2$. The combined organic layers were washed with 1.0N aqu. NaOH and water, then dried over MgSO$_4$. Removal of the solvent in vacuo and vacuum distillation of the residue gave the desired product (18.8 g, bp 110°–118° C./0.1 mm Hg).

(b) Ethyl-N-n-heptyl-2-(4-aminomethylphenoxy)-2-methylpropanoate

The product from step (a) (4.72 g) was dissolved in absolute ethanol (140 ml) and n-heptylamine (2.3 g, Aldrich) added. The resulting solution was refluxed for one hour, 10% Pd/C added and the suspension placed on a Paar hydrogenation apparatus—uptake of hydrogen ceased after approximately ten minutes. The suspension was filtered and the filtrate evaporated in vacuo to give the desired product as a clear oil (6.2 g).

(c) N-(2,4-Dimethoxyphenyl)-N'-heptyl-N'-{p-[2-(carbethoxy)isoprooxy]phenyl}methylurea The product from step (b) (3.49 g) was dissolved in $CH_2Cl_2$ (100 ml) and 2,4-dimethoxyphenylisocyanate (1.9 g, Aldrich) added. The resulting solution was stirred for 8 hours and then evaporated in vacuo. The residue was flash chromatographed through a silica column using hexanes/$CH_2Cl_2$/EtOAc (38:31:31) as eluant to give the desired product as a colourless oil (4.9 g).

(d) N-(2,4-Dimethoxyphenyl)-N'-heptyl-N'-{p-[2-(carboxy)isopropoxy]phenyl}methylurea The product from step (c) (4.85 g) was dissolved in ethanol (25 ml) and 1.0N aqu. NaOH (15 ml) added. The resulting solution was heated to effect dissolution and then refluxed for 4 hours. After cooling, $CH_2Cl_2$ (100 ml) and 1.0N aqu. HCl (60 ml) were added. The organic layer was separated and the aqueous layer extracted with additional $CH_2Cl_2$. The combined organic layers were washed with water, dried over $MgSO_4$ and evaporated in vacuo to leave a pale yellow viscous oil which upon crystallization from hexanes/ether gave the desired product as a colourless solid (2.1 g), mp 80°–81° C.

$^1$H NMR (500 MHz, δ, $CDCl_3$): 6.33–8.04 (m, 8H, aromatic, NH), 4.44 (s, 2H, C$\underline{H}_2$-phenyl, 3.61/3.69 (2×s, 6H, 2,4-$(OCH_3)_2$), 3.26 (t, 2H, N—C$\underline{H}_2$—$(CH_2)CH_3$) and 0.65–1.80 (m, 19H, $(CH_2)_5CH_3$, $(CH_3)_2C$)

FAB MS: $(M-1)^+$=485

Elemental analysis ($C_{27}H_{38}N_2O_6$): C 66.57% (66.64%), H 7.90% (7.87%), N 5.72% (5.76%)

SYNTHETIC EXAMPLE 2

Preparation of 2-(4-{2-[3-(2,4-dimethoxyphenyl)-1-heptylureido]ethyl}phenoxy)-2-methylpropionic acid (a) Carbobenzyloxytyramine Sodium bicarbonate (12.6 g) was dissolved in distilled water (250 ml) and tyramine (20.6 g) added. The resulting suspension was heated to boiling to dissolve the tyramine, then cooled to room temperature. Benzyl chloroformate (25.6 g) was added while stirring and with occasional vigorous shaking. After stirring and shaking for an additional 1.5 hours, the precipitate was filtered off and washed with distilled water. The solid was dissolved in ether (250 ml) and washed with distilled water. The organic layer was dried over $MgSO_4$ and evaporated in vacuo to give a residue which solidified upon cooling. Recrystallization from ether/hexane gave the desired product as colourless crystals, m.p. 96°–98° C.

(b) Ethyl 2-[4-(2-carbobenzyloxyamino)ethyl]phenoxy-2-methylpropanoate

The product from step (a) (42.8 g) and KOH (6.2 g) were dissolved with warming in absolute ethanol (600 ml). Ethyl 2-bromoisobutyrate (21.7 g) was added and the resulting solution refluxed for 5.5 hours. Additional KOH (4.0 g) and ethyl 2-bromosiobutyrate (11.3 g) were then added and refluxing continued for 16.5 hours. After cooling, the precipitated KBr was removed by filtration and the filtrate evaporated in vacuo to give a light brown oil. The oil was dissolved in $CH_2Cl_2$ (500 ml), washed with 1.0N aqu. NaOH, satd. aqu. NaCl 1.0N aqu. HCl and satd. aqu. NaCl, dried over $MgSO_4$ and the solution evaporated in vacuo. The residue was flash chromatographed through a silica column using hexanes/$CH_2Cl_2$/EtOac (50:25:25) as eluant to give the desired product as a colourless oil (23.5 g).

(c) Ethyl 2-[4-(2-aminoethyl)phenoxy]-2-methylpropionate

The product from step (b) (2.7 g) was dissolved in ethanol (100 ml) and 10% Pd/C (0.3 g) added. Paar hydrogenation for 45 minutes resulted in a drop in bottle pressure from 48.5 to 41.0 psi. The Pd/C was removed by filtration and the filtrate evaporated in vacuo to give the desired product as a colourless oil (1.5 g).

(d) Ethyl 2-[4-(heptylaminoethyl)phenoxy]-2-methylpropionate

The product from step (c) (1.5 g) and heptaldehyde (0.7 g) were mixed together in a observably exothermic reaction and the product dissolved in absolute ethanol (100 ml). Paar hydrogenation for 1.0 hour resulted in a drop in bottle pressure from 49.0 to 42.7 psi. The Pd/C was removed by filtration and the filtrate evaporated in vacuo to give the desired product as a colourless oil (2.1 g).

(e) Ethyl 2-(4-{2-[3-(2,4-dimethoxyphenyl)-1-heptylureido]ethyl}phenoxy)-2-methylpropionate The product from step (d) (2.1 g) and 2,4-dimethoxyphenylisocyanate (1.1 g, Aldrich) were dissolved in $CH_2Cl_2$ (50 ml). The resulting solution was stirred at room temperature for 17 hours and then evaporated in vacuo. The residue was flash chromatographed through a silica column using hexanes/$CH_2C_1$/EtOAc (50:25:25) as eluant to give the desired product as a very light brown oil (2.0 g).

(f) 2-(4-{2-[3-(2,4-Dimethoxyphenyl)-1-heptylureido]ethyl}phenoxy)-2-methylpropionic acid The product from step (e) (2.0 g) was dissolved in absolute ethanol (50 ml) and 1.0N aqu. NaOH (30 ml) added. The resulting solution was refluxed for 0.5 hour, cooled to room temperature, acidified with 2.0N aqu. HCl (100 ml) and extracted with $CH_2Cl_2$. The combined organic layers were washed with water and satd. aqu. NaCl, dried over $MgSO_4$ and evaporated in vacuo to give a viscous yellow oil. Repeated recrystallization from ether/hexanes gave the desired product as colourless crystals (1.5 g), mp 95°–96° C.

$^1$H NMR (500 MHz, δ, $CDCl_3$) 6.44–7.99 (m, 7H, aromatic), 3.82 (s, 3H, $OCH_3$), 3.76 (s, 3H, $OCH_3$), 3.45 (t, 2H, $CH_2$), 3.18 (s, 3H, $CH_2$), 2.84 (s, 3H, $CH_2$), 1.55–1.58 (m, 8H, $C(CH_3)_2$, $CH_2$), 1.26–1.30 (m, 8H, $(CH_2)_4$) and 0.86 (t, 3H, $(CH_2)_6C\underline{H}_3$)

FAB MS: $(M-1)^+$=499

Elemental analysis ($C_{28}H_{40}N_2O_6$): C 67.28% (67.17%), H 8.10% (8.05%), N 5.57% (5.60%)

SYNTHETIC EXAMPLE 3

Preparation of 2-(4-{2-[3-(2,4-difluorophenyl)-1-heptylureido]ethyl}phenoxy)-2-methypropionic acid (a) Ethyl 2-[4-(heptylaminoethyl)phenoxy]-2-methylpropionate As for steps (a) to (d) of Synthetic Example 2.

(b) Ethyl 2-(4-{2-[3-(2,4-difluorophenyl)-1-heptylureido]ethyl}phenoxy)-2-methylpropionate The product from step (d) (3.3 g) was dissolved in $CH_2Cl_2$ (100 ml) and 2,4-difluorophenylisocyanate (1.6 g, Aldrich) added. The resulting solution was stirred overnight at room temperature and then evaporated in vacuo. The residue was flash chromatographed through a silica column using toluene/hexanes/$CH_2Cl_2$/EtOAc (50:30:10:10) as eluant to give the desired product as a colourless oil (4.8 g).

(c) 2-(4-{2-[3-(2,4-Difluorophenyl)-1-heptylureido] ethyl}phenoxy)-2-methylpropionic acid The product from step (e) (2.4 g) was dissolved in absolute ethanol (25 ml) and 1.0N aqu. NaOH (10 ml) added. The resulting solution was stirred at room temperature for 3.7 hours, acidified with 1.0M aqu. HCl (100 ml) and extracted with $CH_2Cl_2$. The combined organic layers were washed with brine (50 ml), dried over $MgSO_4$ and evaporated in vacuo to give a colourless oil which was flash chromatographed through a silica column using hexanes/$CH_2Cl_2$/EtOAc (50:25:25) as eluant to give the desired product as a very pale yellow viscous oil (1.4 g).

$^1$H NMR (500 MHz, δ, $CDCl_3$): 6.77–7.99 (m, 6H, aromatic), 6.27 (s, 1H, NH), 4.10 (q, 4H, $OCH_2$), 3.48 (t, 2H, $CH_2$), 3.19 (t, 2H, $CH_2$), 2.84 (t, 2H, $CH_2$), 1.59 (m, 2H, $CH_2$), 1.53 (s, 6H, $(CH_3)_2C$), 1.22–1.28 (m, 10H, $(CH_2)_5$) and 0.86 (t, 3H, $(CH_2)_6C\underline{H}_3$)

FAB MS: $(M-1)^+=475$

Elemental analysis ($C_{26}H_{34}F_2N_2O_4$): C 65.65% (65.53%), H 7.24% (7.19%), N 5.86% (5.88%).

SYNTHETIC EXAMPLES 4–98

The following compounds of formula (I) were prepared by methods analogous to those of Synthetic Examples 1 to 3. All compounds have $^1$H NMRs and elemental analyses consistent with the proposed structures.

4) Ethyl 2-{4-[3-(4-chlorophenyl)-1-heptylureidomethyl] phenoxy}-2-mehylpropionate, mp 46°–48° C.;

5) 2-{4-[3-(4-Chlorophenyl)-1-heptylureidomethyl] phenoxy}-2-methylpropionic acid, mp 120°–122° C.;

6) Ethyl 2-[N'-(4-chloro-2-trifluoromethylphenyl)-N-heptylureidomethylphenoxy]-2-methylpropionate, colourless oil;

7) Ethyl 2-(4-{[1-heptyl-3-(2,4,6-trichlorophenyl)ureido]methyl}phenoxy)-2-methylpropionate, pale yellow liquid;

8) 2-(4-{[1-Heptyl-3-(2,4,6-trichlorophenyl)ureido]methyl}phenoxy)-2-methylpropionic acid, mp 52°–54°C.;

9) Ethyl 2-[3-(2,4-difluoro-6-methoxyphenyl)-1-heptylureidomethylphenoxy]-2-methylpropionate, colourless oil;

10) 1-(2,4-Difluoro-6-methoxyphenyl)-3-[4-(2-hydroxy-1,1-dimethylethoxy)benzyl]urea, colourless oil;

11) 2-{4-(3-(2-Ethoxyphenyl)-1-heptylureidomethyl] phenoxy}-2-methylpropanol, pale tan oil;

12) 2-{[3-(2,4-Dimethoxyphenyl)-1-heptylureido] methyl}phenoxy)propionic acid, mp 98°–99° C.;

13) Ethyl 5-(4-{[3-(2,4-dimethoxyphenyl)-1-heptylureido] methyl}phenoxy-2,2-dimethylvalerate, colourless oil;

14) 2-[4-({1-[2-(4-Chlorophenyl)ethyl]-3-(2,4-dimethoxyphenyl)ureido}methyl)phenoxy]-2-methylpropionic acid, mp 118.5°–120° C.;

15) (4-{[3-(2,4-Dimethoxyphenyl)-1-octylureido]methyl}phenoxy)-2-methylpropionic acid, mp 62°–64° C.;

16) Ethyl (4-{[3-(2,4-dimethoxyphenyl)1-pentylureido]methyl}phenoxy)-2-methylpropionate, yellow oil;

17) 2-(4-{[3-(2,4-Dimethoxyphenyl)-1pentylureido]methyl}phenoxy)-2-methylpropionic acid, mp 119°–120° C.;

18) 2-(4-{[1-(3,3-Dimethylbuzyl)-3-(2,4-dimethoxyphenyl) ureido]methyl}phenoxy)-2-methylpropionic acid, mp 149°–150° C.;

19) 1-Heptyl-1-[4-(2-hydroxy-1,1-dimethylethoxy)benzyl]-3-(2,4,6-trimethoxyphenyl)urea, mp 109°–110° C.;

20) 3-(2,4-Dimethoxyphenyl)-1-heptyl-1-[4-(2-hydroxy-1-methylethoxy)benzyl]urea, colourless oil;

21) Ethyl 2-[4-(N'-2-biphenylyl-N-heptylureidomethyl) phenoxy]-2-methylpropionate, mp 61°–62° C.;

22) 2-{4-[3-(2-Biphenylyl)-1-heptylureidomethyl] phenoxy}-2-methylpropionic acid 0.75 potassium salt, no mp (amorphous solid);

23) Ethyl 2-{4-[1-heptyl-3-(2-phenoxyphenyl)ureidomethyl]phenoxy}-2-methylpropionate, pale tan gum;

24) 3-(2,4-Dimethoxyphenyl)-1-heptyl-1-{4-[(5-hydroxy-4,4-dimethylpentyl)oxy]benzyl}urea, colourless oil;

25) Ethyl 2-{4-[3-(2-ethoxy-4,6-difluorophenyl)-1-heptylureidomethyl]phenoxy}-2-methylpropionate, colourless oil;

26) Ethyl 2-{4-[3-(4-chloro-2-ethoxyphenyl)-1-heptylureidomethyl]-phenoxy}-2-methylpropionate, colourless oil;

27) Ethyl 2-(4-{[3-(2,4-dimethoxyphenyl)-1-heptylureido] methyl}phenoxy)-2-methylpropionate, colourless oil;

28) Ethyl 2-(4-{[3-(5-chloro-2,4-dimethoxyphenyl)-1-heptylureido]methyl}phenoxy)-2-methylpropionate, yellow oil;

29) Ethyl 2-{4-[3-(2-ethoxy-1-naphthyl)-1-heptylureidomethyl]phenoxy}-2-methylpropionate, mp 89°–91° C.;

30) Ethyl 2-[N'-(2,5-di-t-butylphenyl)-N-heptylureidomethylphenoxy]-2-methylpropionate, mp 82.5°–84.5° C.;

31) 2-{4-[3-(2-Biphenylyl)-1-heptylureidomethyl] phenoxy}-2-methylpropanol, colourless oil;

32) Ethyl 2-{4-[3-(4-fluorenyl)-1-heptylureidomethyl] phenoxy}-2-methylpropionate, mp 78°–79° C.;

33) Ethyl 2-{[3-(2-fluorophenyl)-1-heptylureidomethyl] phenoxy}-2-methylpropionate, colourless oil;

34) Ethyl 2-{4-[3-(2,6-difluorophenyl)-1-heptylureidomethyl]phenoxy}isobutyrate, colourless oil;

35) Ethyl 2-{4-[3-(2,4-difluorophenyl)-1-heptylureidomethyl]phenoxy}-2-methylpropionate, colourless oil;

36) Ethyl 2-[4-(2,4-difluoro-N-heptylphenylacetamidomethyl)phenoxy]-2-methylpropionate, very pale yellow oil;

37) Ethyl 2-{4-[1-t-butyl-3-(2,4-difluorophenyl) ureidomethyl]phenoxy}-2-methylpropionate, mp 80°–82° C.;

38) Ethyl 5-{4-[3-(2,4-difluorophenyl)-1-heptylureidomethyl]phenoxy}valerate, colourless oil;

39) Ethyl 2-(4-{3-[2-(4-t-butylbenzyloxy)-4,6-difluorophenyl]-1-heptylureidomethyl}phenoxy)-2-methylpropionate, colourless oil;

40) Ethyl 2-{N'-[2-(4-t-butylbenzyloxy)phenyl]-N-heptylureidomethyl}phenoxy-2-methylpropionate, colourless oil;

41) Ethyl 2-(4-{N'-[2-(4-t-butylbenzyloxy)-4-chlorophenyl]-N-heptylureidomethyl}phenoxy)-2-methylpropionate, mp 76°–78° C.;

42) Ethyl 2-(4-{[(4-chlorophenoxy)carbonyl] heptylaminomethyl}phenoxy)-2-methylpropionate, no mp (amorphous solid);

43) Ethyl 2-{4-[3-(4-chlorophenyl)-1-dodecylureidomethyl] phenoxy}-2-methylpropionate, yellow oil;

44) Ethyl 2-(4-{[(4-chlorophenoxy)carbonyl] dodecylaminomethyl}phenoxy)-2-methylpropionate, colourless viscous oil;

45) Ethyl 5-{4-[3-(4-chlorophenyl)-1-heptylureidomethyl]phenoxy}valerate, colourless oil;
46) 1-(4-Chloro-2-trifluoromethylphenyl)-3-heptyl-3-[4-(2-hydroxy-2,2-dimethylethoxy)benzyl]urea, colourless oil;
47) 2-{4-[3-(2,4-Dichlorophenyl)-1-heptylureidomethyl]phenoxy}-2-methylpropionic acid, mp 73°–74.5°–° C.;
48) Ethyl 2-{4-[3-(3,4-dichlorophenyl)-1-heptylureidomethyl]phenoxy}-2-methylpropionate, no mp (colourless wax);
49) Ethyl 2-{4-[1-dodecyl-3-(2,4,6,-trichlorophenyl)ureidomethyl]phenoxy)-2-methylpropionate, colourless oil;
50) Ethyl 2-{4-[3-(4-chloro-2-nitrophenyl)-1-heptylureidomethyl]phenoxy}-2-methylpropionate, yellow oil;
51) Ethyl 2-{4-[1-heptyl-3-(2-methoxyphenyl)ureidomethyl]phenoxy}-2-methylpropionate, yellow oil;
52) Ethyl {4-[3-(4-methoxyphenyl)-1-heptylureidomethyl]phenoxy}-2-methylpropionate, no mp (colourless wax);
53) Ethyl 2-{4-[1-heptyl-3-(2-trifluoromethoxyphenyl)ureidomethyl]phenoxy}-2-methylpropionate, colourless oil;
54) Ethyl 2-(4-{3-[2-fluoro-6(2,2,2-trifluoroethoxy)phenyl]-1-heptylureidomethyl}phenoxy)-2-methylpropionate, pale tan oil;
55) 2-{4-[3-(4-Chloro-2-methoxyphenyl)-1-heptylureidomethyl]phenoxy}-2-methylpropionic acid, mp 121°–122° C.;
56) Ethyl 2-{4-[1-heptyl-3-(2-methylthiophenyl)ureidomethyl]phenoxy}-2-methylpropionate, colourless oil;
57) Ethyl 2-{4-[N'-(2-Ethoxyphenyl)-N-heptylureidomethyl]phenoxy}-2-methylpropionate, colourless oil;
58) Ethyl 2-{4-[3-(2,4-dichloro-6-ethoxyphenyl)-1-heptylureidomethyl]phenoxy}-2-methylpropionate, colourless oil;
59) 2-Ethoxyphenyl N-[4-(1-ethoxycarbonyl-1-methylethoxy)benzyl]-N-heptylcarbamate, colourless oil;
60) Ethyl 2-(4-[1-heptyl-3-(2-propoxyphenyl)ureidomethyl]phenoxy}-2-methylpropionate, colourless oil;
61) Ethyl 2-{4-[3-(2,6-dimethoxyphenyl)-1-heptylureidomethyl]phenoxy}-2-methylpropionate, colourless oil;
62) Ethyl 2-[4-(N-heptyl-2,4-dimethoxyphenylacetamidomethyl)phenoxy]-2-methylpropionate, pale tan oil;
63) 2-{4-[3-(2,4-Dimethoxyphenyl)-1heptylureidomethyl]phenoxy}butyric acid, pale yellow oil;
64) 3-(2,4-Dimethoxyphenyl)-1-heptyl-1-[4-(1-hydroxymethylpropoxy)benzyl]urea, tan oil;
65) 5-{4-[3-(2,4-Dimethoxyphenyl)-1-heptylureidomethyl]phenoxy}-2,2-dimethylvaleric acid, tan oil;
66) 2-{4-[1-Heptyl-3-(2,4,6-trimethoxyphenyl)ureidomethyl]phenoxy}-2-methylpropionic acid, mp 140°–142° C.;
67) Ethyl 2-(4-{1-[2-(4-chlorophenyl)ethyl]-3-(2,4-dimethoxyphenyl)ureidomethyl}phenoxy)-2-methylpropionate, mp 89.5°–91° C.;
68) 2-{4-[3-(2,4-Dimethoxyphenyl)-1nonylureidomethyl]phenoxy}-2-methylpropionic acid, mp 55°–57° C.;
69) Ethyl 2-{4-[3-(2,4-dimethoxyphenyl)-1propylureidomethyl]phenoxy}-2-methylpropionate, mp 69°–71° C.;
70) 2-{4-[3-(2,4-Dimethoxyphenyl)-1-propylureidomethyl]phenoxy}-2-methylpropionic acid, mp 96°–98° C.;
71) Ethyl 2-{4-[1-t-butyl-3-(2,4-dimethoxyphenyl)ureidomethyl]phenoxy}-2-methylpropionate, mp 80°–816° C.;
72) Ethyl 2-{4-[3-(2,4-difluoro-6-methoxyphenyl)-1-(1,1-dimethyloctyl)ureidomethyl]phenoxy}-2-methylpropionate, mp 57–59° C.;
73) Ethyl 2-{4-[3-(2,4-dimethoxyphenyl)-1(1,1-dimethoxyhexyl)ureidomethyl]phenoxy}-2-methylpropionate, pale tan oil;
74) Ethyl 2-{4-[3-chloro-2-thienyl)-1-heptylureidomethyl]phenoxy}-2-methylpropionate, yellow-tan oil;
75) 3-(2,4-Dimethoxyphenyl)-1-heptyl-1-{2-[4-(2-hydroxy-1,1-dimethylethoxy)phenyl]ethyl}urea, tan oil;
76) 2-(4-{2-[1-Heptyl-3-(2,4,6-trimethoxyphenyl)ureido]ethyl}phenoxy)-2-methylpropionic acid, mp 100°102° C.;
77) 2-(4-{2-[1-Heptyl-3-(2,4,6-trimethylphenyl)ureido]ethyl}phenoxy)-2-methylpropionic acid, mp 53°–103° C. (glass);
78) 2-(4-{2-[1-Heptyl-3-(2,4,6-trichlorophenyl)ureido]ethyl}phenoxy)-2-methylpropionic acid, mp 47°–55° C.;
79) 2-(4-{2-[3-(2,6-Diisopropylphenyl)-1-heptylureido]ethyl}phenoxy)-2-methylpropionic acid, mp 56°–57° C.;
80) 1-{2-[4-(2-Hydroxy-1,1,-dimethylethoxy)phenyl]ethyl}-3-(2,4-dimethoxyphenyl)-1-(6,6-dimethylheptyl)urea, colourless oil;
81) 2-(4-{2-[3-(2,4-Dimethoxyphenyl)-1-(3,3-dimethylbutyl)ureido]ethyl}phenoxy)-2-methylpropionic acid, 145°–147° C.;
82) 5-(4-{2-[3-(2,4-Dimethoxyphenyl)-1-heptylureido]ethyl}phenoxy)-2,2-dimethylvaleric acid, tan oil;
83) 2-(4-{3-[3-(2,4-Dimethoxyphenyl)-1heptylureido]propyl}phenoxy)-2-methylpropionic acid, yellow oil;
84) Ethyl 2-(4-[1-heptyl-3-(2-tolyl)ureidomethyl]phenoxy}-2-methylpropanoate, colourless oil;
85) Ethyl 2-{4-[N'-(2,6-dimethylphenyl)-N-heptylureidomethyl]phenoxy}-2-methylpropionate, mp 68°–70° C.;
86) Ethyl 2-{4-[N'-(4-bromo-2,6-dimethylphenyl)-N-heptylureidomethyl]phenoxy}-2-methylpropionate, mp 72°–74° C.;
87) Ethyl 2-{4-[1-heptyl-3-(2-isopropylphenyl)ureidomethyl]phenoxy}-2-methylpropionate, mp 38°–39° C.;
88) Ethyl 2-{4-[1-heptyl-3-(2-isopropyl-6-methylphenyl)ureidomethyl]phenoxy}-2-methylpropionate, mp 88°–90° C.;
89) Ethyl 2-{4-[3-(2,6-diisopropylphenyl)-1-heptylureidomethyl]phenoxy}-2-methylpropionate, mp 135°–136° C.;
90) Ethyl 2-{4-[1-heptyl-3-(1-methoxy-2-naphthyl)ureidomethyl]phenoxy}-2-methylpropionate, pale green oil;
91) Ethyl 2-(4-{1-[2-fluoro-6-(4-pivaloylbenzyloxy)]-3-heptylureidomethyl}phenoxy)-2-methylpropionate, colourless oil;
92) Ethyl 2-(4-{3-[2-(4-t-butylbenzyloxy)-4-methoxyphenyl]-1-heptylureidomethyl}phenoxy)-2-methylpropionate, pale tan oil;
93) Ethyl 2-[4-(3-{2-fluoro-6-[4-(1-hydroxy-2,2-dimethylpropyl)benzyloxy]phenyl}-1-heptylureidomethyl)phenoxy]-2-methylpropionate, almost colourless oil;
94) Ethyl 2-(4-{3-[2,4-dichloro-6-(4-pivaloylbenzyloxy)phenyl]-1-heptylureidomethyl}phenoxy)-2-methylpropionate, pale yellow gum;
95) 3-(2,4-Dimethoxyphenyl)-1heptyl-1-[4-(2-hydroxy-1,1-dimethylethoxy)benzyl]urea, yellow oil;
96) 2-{4-[3-(2,4-Difluorophenyl)-1-heptylureidomethyl]phenoxy}-2-methylpropionic acid, no mp (amorphous solid);
97) Ethyl 2-{4-[3-(2-cyclohexylmethoxy-4-methoxyphenyl)-1-heptylureidomethyl]phenoxy}-2-methylpropionate, pale tan oil; and 98) 2-(4-{2-[3-(2,4-Dimethoxyphenyl)ureido]ethyl}phenoxy)-2-methylpropionic acid, mp 159°–160° C.

Pharmaceutical Formulation Examples

In the following Examples, the "active ingredient" is any compound of formula (I) as hereinbefore defined, preferably one of the compounds of Synthetic Examples 1 to 98.

| Tablet | |
| --- | --- |
| | Per tablet |
| Active Ingredient | 5.0 mg |
| Lactose | 82.0 mg |
| Starch | 10.0 mg |
| Povidone | 2.0 mg |
| Magnesium Stearate | 1.0 mg |

Mix together the active ingredient, lactose and starch. Granulate the powders using a solution of povidone in purified water. Dry the granules, add the magnesium stearate and compress to produce 100 mg tablets.

| Controlled release tablet | |
| --- | --- |
| | Per tablet |
| Active ingredient | 500 mg |
| Hydroxypropylmethylcellulose (Methocel K4M Premium) | 112 mg |
| Lactose B.P. | 53 mg |
| Povidone B.P.C. | 28 mg |
| Magnesium Stearate | 7 mg |
| | 700 mg |

The formulation may be prepared by wet granulation of the first three ingredients with the solution of povidone, followed by addition of the magnesium stearate and compression.

| Capsule | |
| --- | --- |
| | Per capsule |
| Active ingredient | 250 mg |
| Lactose B.P. | 143 mg |
| Sodium Starch Glycollate | 25 mg |
| Magnesium Stearate | 2 mg |
| | 420 mg |

Capsules may be prepared by admixing the ingredients of the formulation and filling two-part hard gelatin capsules with the resulting mixture.

| Controlled release capsule | |
| --- | --- |
| | Per capsule |
| Active ingredient | 250 mg |
| Microcrystalline Cellulose | 125 mg |
| Lactose B.P. | 125 mg |
| Ethyl Cellulose | 13 mg |
| | 513 mg |

The controlled-release capsule formulation may be prepared by extruding a mixture of the first three ingredients, then spheronising and drying the extrudate. The dried pellets are coated with the ethyl cellulose as a controlled-release membrane and filled into two-part hard gelatin capsules.

| Powder capsule for inhalation | |
| --- | --- |
| | Per capsule |
| Active Ingredient (0.5–7.0 μm powder) | 4.0 mg |
| Lactose (30–90 μm powder) | 46.0 mg |
| | 50.0 mg |

The powders were mixed until homogeneous and filled into suitably sized hard gelatin capsules (50 mg per capsule).

| Injectable solution | |
| --- | --- |
| Active ingredient | 101 mg |
| Glycerol formal | 3.5 ml |

The active ingredient was dissolved in the glycerol formal by shaking the mixture for 2–3 minutes. The resulting solution was distributed into ampoules under aseptic conditions.

| Oral solution A | |
| --- | --- |
| Active ingredient | 414 mg |
| Glycerol formal | 7.0 ml |

The active ingredient was dissolved in the glycerol formal by shaking the mixture for 2–3 minutes. The resulting solution was distributed into ampoules under aseptic conditions.

| Oral solution B | |
| --- | --- |
| Active ingredient | 179 mg |
| Labrafil M1944 CS (Gattefosse) | 7.0 ml |

The active ingredient was dissolved in the Labrafil M1944 CS by stirring the mixture at 40°–45° C. for 5–10 minutes. The resulting solution was distributed into ampoules under aseptic conditions.

| Intramuscular injection formulation | |
| --- | --- |
| Active ingredient | 0.20 g |
| Benzyl Alcohol | 0.10 g |
| Glycofurol 75 | 1.45 g |
| Water for Injection q.s. to | 3.00 ml |

The active ingredient is dissolved in the glycofurol. The benzyl alcohol is added and dissolved, then water added to 3 ml. The solution is filtered through a sterile micropore filter and sealed in sterile 3 ml glass vials.

| Inhalation aerosol | |
| --- | --- |
| Active Ingredient (0.5–7.0 μm powder) | 200 mg |
| Sorbitan Trioleate | 100 mg |
| Saccharin Sodium (0.5–7.0 μm powder) | 5 mg |
| Methanol | 2 mg |
| Trichlorofluoromethane | 4.2 g |
| Dichlorodifluoromethane to | 10.0 ml |

The sorbitan trioleate and menthol are dissolved in the trichlorofluoromethane. The saccharin sodium and active ingredient are dispersed in the mixture which is then transferred to a suitable aerosol canister and the dichlorofluoromethane injected through the valve system. This composition provides 2 mg of active ingredient in each 100 μl dose.

| Syrup formulation | |
|---|---|
| Active ingredient | 0.25 g |
| Sorbitol Solution | 1.50 g |
| Glycerol | 1.00 g |
| Sodium Benzoate | 0.0050 g |
| Flavour | 0.0125 ml |
| Purified Water q.s. to | 5.0 ml |

The sodium benzoate is dissolved in a portion of the purified water and the sorbitol solution added. The active ingredient is added and dissolved. The resulting solution is mixed with the glycerol and then made up to the required volume with the purified water.

| Suppository formulation | |
|---|---|
| | Per suppository |
| Active ingredient (63 μm)* | 250 mg |
| Hard Fat, BP (Witepsol H15 - Dynamit Nobel) | 1770 mg |
| | 2020 mg |

*The active ingredient is used as a powder wherein at least 90% of the particles are of 63 μm diameter or less.

One-fifth of the Witepsol H15 is melted in a steam-jacketed pan at a maximum temperature of 45° C. The active ingredient is sifted through a 200 μm sieve and added to the molten base with mixing, using a Silverson fitted with a cutting head, until a smooth dispersion is achieved. Maintaining the mixture at 45° C., the remaining Witepsol H15 is added to the suspension which is stirred until homogenous. The entire suspension is then passed through a 250 μm stainless steel screen and allowed to cool to 40° C. with continuous stirring. At a temperature of 38°–40° C., 2.0 g aliquots of the mixture are filled into suitable plastic moulds and the suppositories allowed to cool to room temperature.

| Pessary formulation | |
|---|---|
| | Per pessary |
| Active ingredient (63 μm) | 250 mg |
| Anhydrous Dextrose | 380 mg |
| Potato Starch | 363 mg |
| Magnesium Stearate | 7 mg |
| | 1000 mg |

The ingredients are mixed directly and pessaries prepared by compression of the resulting mixture.

Biologcal Assays (i) In vitro assay for the inhibition of ACAT activity

ACAT activity was determined as described By Ross et al by the incorporation of [$^{14}$C]oleoyl-CoA into cholesterol [$^{14}$C]oleate using hepatic microsomes as the source of both ACAT and cholesterol. Microsomes were prepared from the livers of male CD rats fed a 0.4% cholesterol/0.2% cholic acid diet 3.5 days before sacrifice. Various concentrations of a test compound were preincubated with a 0.5 mg/ml microsomal suspension and after 15 minutes a 50 μg aliquot was removed and incubated with 25 μM of [$^{14}$C]-enriched oleoyl-CoA for 4 minutes. The reaction was terminated by the addition of 1 ml of ethanol and 4 ml of hexane. After shaking, the hexane layer was removed and evaporated to dryness. The hexane extract was then reconstituted in 150 μl of HPLC solvent and injected on to a B&J OD5 Reverse Phase C18 column using an isocratic mobile phase of acetonitrile: isopropanol:heptane (50:40:10) in 0.5% acetic acid at a flow rate of 1.0 ml/min. The product of the reaction, [$^{14}$C]oleoyl cholesterol, was measured using a Flow One radiometric detector. The ACAT $IC_{50}$ value for each compound was determined from a plot of % inhibition from control vs inhibitor concentration.

The $IC_{50}$s for the compounds of Synthetic Examples 1 to 3 were 4.5 μM, 3.4 μM and 7.6 μM respectively.

(ii) Determination of hypolipdemic activity in cholesterol-cholic acid fed rats

Male Sprague-Dawley rats (CD, Charles River) each weighing 200–300 g were used. Hypercholesterolemia was induced in the rats by administration of a diet enriched to 0.4% cholesterol, 0.2% cholic acid. Prior to the adminstration of the diet, blood samples were collected under halothane anesthesia by cardiac puncture to determine baseline lipid levels. The blood was allowed to clot and serum was obtained for the analysis of total cholesterol, dextran-precipitable lipoproteins cholesterol (VLDL+LDL) and total triglycerides. The rats were divided into groups so that each group had similar average baseline serum lipid levels. Five days after the initial blood sampling, administration of each test compound and the cholesterol-cholic acid-enriched diet was begun. Compounds to be tested by gavage were administered b.i.d. in either 0.5% methyl cellulose or 5% sodium bicarbonate a 9:00 a.m. and 3:00 p.m. for three days and at 9:00 a.m. on the fourth day. Compounds administered as part of the diet were dissolved in ethanol and sprayed on to the diet. The ethanol was allowed to evaporate and the diet given to the rats for three days. On the fourth day, blood samples were collected and the final serum lipid levels determined. All blood samplings were taken after a four-hour fast.

The compound of Synthetic Example 1 at a dose of 25 mg/kg reduced LDL-cholestrol by 55% and at a dose of 50 mg/kg by 67%. The corresponding figures for the compound of Synthetic Example 2 were 5 mg/kg (41–71%) and 25 mg/kg (61%) and for the compound of Synthetic Example 3 were 0.5 mg/kg (90%) and 2 mg/kg (74%).

We claim:

1. A compound of formula (I)

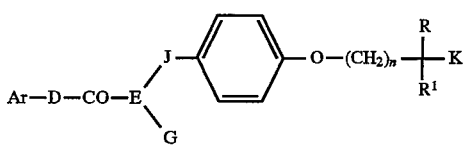

wherein

Ar is a phenyl group optionally containing one or two heteroatoms independently selected from nitrogen, oxygen, sulfur, said group being optionally substituted by one or more atoms or groups independently selected from halogen, nitro, amino, —NRR$^1$ where R and R$^1$ are independently selected from hydrogen, $C_{1-8}$ alkyl and $C_{1-8}$ alkanoyl, cyano, carboxyalkoxy, alkoxycarbonylalkoxy, $C_{1-8}$ alkyl (including cycloalkyl and cycloalkylalkyl), $C_{1-8}$ alkoxy (including cycloalkoxy and cycloalkylalkoxy), $C_{1-8}$ thioalkyl, said alkyl, alkoxy and/or thioalkyl group(s) being optionally substituted by one or more halogen atoms, aryl, aryloxy, aralkyl and aralkyloxy, said aryl, aryloxy, aralkyl, and/or aralkyloxy group(s) being optionally substituted by one or more atoms or groups independently selected from halogen, alkyl, alkoxy, alkanoyl, hydroxyalkyl, perfluroalkyl, perfluoroalkoxy, carboxyalkoxy, alkoxycarbonylalkoxy, and $C_{3-8}$ polyether groups containing from one to three oxygen atoms;

D is —$CH_2$—, —NH— or —O—;

E is —N= or CH=;

G is $C_{1-12}$ straight, branched, or cyclic alkyl, or aralkyl, said aralkyl group being optionally substituted by one or more atoms or groups independently selected from halogen, amino N-($C_{1-6}$ alkyl)amino, N,N-di($C_{1-6}$ alkyl)amino, $C_{1-6}$ alkyl and $C_{1-6}$ alkoxy, or a $C_{3-8}$ polyether group containing one to three oxygen atoms;

J is a $C_{1-6}$ straight or branched alkylene;

n is an integer from 0 to 10;

R and $R^1$ are as hereinbefore defined; and

K is —$CH_2OH$, —CHO, —$CONHCH_2CONH_2$, —CONH($C_{1-6}$ alkyl), —OC($C_{1-4}$ alkyl)$_2$ OCOheteroaryl, $CO_2R^2$ where $R^2$ is hydrogen, $C_{1-8}$ alkyl, aryl, heteroaryl, aralkyl, heteroaralkyl, or a $C_{3-8}$ polyether group containing form one to three oxygen atoms, or —CONHAr' where Ar' is phenyl optionally substituted by one or more atoms or groups selected from fluorine, nitro, —$NRR^1$ where R and $R^1$ are as hereinbefore defined, $C_{1-6}$ alkyl and $C_{1-6}$ alkoxy, said alkyl and/or alkoxy group(s) being optionally substituted at the terminal carbon by —$CO_2R^3$ is $C_{1-6}$ alkyl;

and salts and physiologically functional derivatives thereof.

2. A compound of formula (I) as shown in claim 1, wherein Ar is phenyl substituted by one or more atoms or groups independently selected from halogen, $C_{1-8}$ alkyl, $C_{1-8}$ alkoxy, cycloalkylalkoxy, said alkyl and/or alkoxy group(s) being optionally substituted by one or more halogen atoms, $C_{1-8}$ thioalkyl, aryl, aryloxy and aralkoxy, said aralkoxy group being optionally substituted by alkyl, alkoyl, or hydroxyalkyl;

D is —NH— or —O—;

E is —N<;

G is $C_{5-8}$ straight or branched alkyl, (4-halophenyl)$C_{1-3}$ alkyl, or $C_{1-3}$ alkyl;

J is $C_{1-3}$ alkylene;

n is an integer of from 0 to 4;

R and $R^1$ are respectively hydrogen and $C_{1-4}$ alkyl or are both $C_{1-4}$ alkyl; and K is —$CO_2R^2$ where $R^2$ is hydrogen or $C_{1-4}$ alkyl, or —$CH_2OH$;

and salts physiologically functional derivatives thereof.

3. A compound of formula (I) as claimed in claim 1, which compound is selected from 2-(4-{2-[3-(2,4-dimethoxyphenyl)-1-heptylureido] ethyl}phenoxy)-2-methylpropionic acid, 2-(4-{2-[3-(2,4-difluorophenyl)-1-heptylureido] ethyl}phenoxy)-2-methylpropionic acid;

2-(4-[3-(2,4-dimethoxyphenyl)-1-heptylureidomethyl] phenoxy)-2-methylpropionic acid, 2-{4-[1-heptyl-3-(2,4,6-trichlorophenyl)ureidomethyl] phenoxy}-2-methylpropionic acid, 2-{4-[1-(3,3-dimethylbutyl)-3-(2,4-dimethoxyphenyl) ureidomethyl]phenoxy}-2-methylpropionic acid, 3-(2,4-dimethoxyphenyl)-1-heptyl-1-[4-(2-hydroxy-1-methylethoxy)benzyl]urea, 3-(2,4-dimethylphenyl)-1-heptyl-1-[4-(5-hydroxy-4,4-dimethylpentyloxy)benzyl]urea and their physiologically acceptable salts and physiologically functionally derivatives.

4. A medicament comprising a compound of formula (I) as claimed in any of claims 1 to 3, or a physiologically functional derivative thereof, a pharmaceutically acceptable carrier and, optionally, one or more other physiologically active agents for use in the treatment of a clinical condition for which an ACAT inhibitor and/or a fibrate is indicated.

5. A medicament as claimed in claim 4 which is in the form of a tablet or capsule.

* * * * *